United States Patent
Berlin

(10) Patent No.: US 7,153,671 B2
(45) Date of Patent: Dec. 26, 2006

(54) METHOD FOR RELATIVE QUANTIFICATION OF METHYLATION OF CYTOSINE BASES IN DNA SAMPLES

(75) Inventor: Kurt Berlin, Stahnsdorf (DE)

(73) Assignee: Epigenomics AG, Berlin (DE)

(*) Notice: Subject to any disclaimer, the term of this patent is extended or adjusted under 35 U.S.C. 154(b) by 401 days.

(21) Appl. No.: 10/057,776

(22) Filed: Jan. 25, 2002

(65) Prior Publication Data

US 2003/0032026 A1 Feb. 13, 2003

Related U.S. Application Data

(63) Continuation-in-part of application No. PCT/DE00/02490, filed on Jul. 25, 2000.

(30) Foreign Application Priority Data

Jul. 26, 1999 (DE) ............................... 193 35 772

(51) Int. Cl.
*C12P 19/34* (2006.01)
*C12Q 1/68* (2006.01)

(52) U.S. Cl. .......................................... 435/91.2; 435/6

(58) Field of Classification Search ............. 422/82.01; 435/6, 91.1, 91.2; 536/23.1, 24.3; 356/344
See application file for complete search history.

(56) References Cited

U.S. PATENT DOCUMENTS

| | | | | |
|---|---|---|---|---|
| 5,786,146 A | * | 7/1998 | Herman et al. ................. | 435/6 |
| 5,837,832 A | | 11/1998 | Chee et al. | |
| 6,046,002 A | * | 4/2000 | Davis et al. .................... | 435/6 |
| 6,379,889 B1 | * | 4/2002 | Apffel et al. ................... | 435/6 |

FOREIGN PATENT DOCUMENTS

| | | |
|---|---|---|
| DE | 4212939 A1 | 10/1993 |
| DE | 19754482 A1 | 7/1999 |
| WO | WO 9856952 A1 * | 12/1998 |

OTHER PUBLICATIONS

Wang et al., Large-Scale Identification, Mapping and Genotyping of Single-Nucleotide Polymorphisms in the Human Genome, Science, May 1998, vol. 280, pp. 1077-1082.*
Roche et al., "Capillary Electrophoresis in Biotechnology," Biotechnology Progress, 1997, vol. 13, pp. 659-668.*
Yurov et al., "High resolution multicolor fluorescence in situ hybridization using cyanine and fluorescein dyes: rapid chromosom identification by directly fluorescently labeled alphoid DNA probes," 1996, vol. 97, pp. 390-398.*
Olek et al., "A modified and improved method for bisulphite based cytosine methylation analysis," Nucleic Acids Research, 24(24):5064-6 (1996).
Abstract of Paul et al., "Cytosine methylation: quantitation by automated genomic sequencing and GENESCAN analysis," Biotechniques, 21(1):126-33 (1996).

* cited by examiner

*Primary Examiner*—Young J. Kim
(74) *Attorney, Agent, or Firm*—Kriegsman & Kriegsman

(57) ABSTRACT

A method is described for the relative quantification of the methylation of cytosine bases in DNA samples, wherein the following method steps are conducted:
 a) a genomic DNA sample is chemically converted with a reagent, wherein 5-methylcytosine and cytosine react differently and show a different base pairing behavior in the DNA duplex after the reaction;
 b) the DNA sample is amplified, whereby a fluorescently labeled dCTP or dGTP derivative is added;
 c) the amplified products are separated spatially from each other; and
 d) the fluorescence of the separated amplified products is measured quantitatively.

13 Claims, No Drawings

METHOD FOR RELATIVE QUANTIFICATION OF METHYLATION OF CYTOSINE BASES IN DNA SAMPLES

CROSS-REFERENCE TO RELATED APPLICATIONS

The present application is a continuation-in-part of presently-pending International Application No. PCT/DE00/02490, with an international filing date of Jul. 25, 2000, said application having been published in German under PCT Article 21(2) and being incorporated herein by reference.

BACKGROUND OF THE INVENTION

The invention concerns a method for the relative quantification of methylation of cytosine bases in DNA samples.

5-Methylcytosine is the most frequent covalently modified base in the DNA of eukaryotic cells. For example, it plays a role in the regulation of transcription, genomic imprinting and in tumorigenesis. The identification of 5-methylcytosine is thus as a component of genetic information is of considerable interest. 5-Methylcytosine positions, however, cannot be identified by sequencing, since 5-methylcytosine has the same base pairing behavior as cytosine. In addition, in the case of a PCR amplification, the epigenetic information, which is borne by 5-methylcytosines, is completely lost.

Several methods are known for solving these problems. For the most part, a chemical reaction or enzymatic treatment of genomic DNA is performed, as a consequence of which cytosine can be distinguished from methylcytosine bases. A current method is the reaction of genomic DNA with bisulfite, which leads to a conversion of cytosine bases to uracil after alkaline hydrolysis in two steps (Shapiro, R., Cohen, B., Servis, R. Nature 227, 1047 (1970)). 5-Methylcytosine remains unchanged under these conditions. The conversion of C to U leads to a change in the base sequence, from which the original 5-methylcytosines can now be determined by sequencing (only methylcytosines can still provide a band in the C lane).

An overview of the other known possibilities for detecting 5-methylcytosines can be taken from the following review article together with all of the references cited therein: Rein, T., DePamphilis, M. L., Zorbas, H., Nucleic Acids Res. 26, 2255 (1998).

In the method described in DE 197 54 482 A1, knowledge of the frequency of methylation in a fragment is not directly obtained, but rather an abstract pattern is first obtained, the components of which need not necessarily belong to the initial fragments.

Paul, C. L. et al. (Biotechniques (1996) 21 (1) 126–33: Cytosine methylation: quantitation by automated genomic sequencing and GENESCAN analysis) describes a method of sequencing with the use of thymine and cytosine bases that are labeled differently. Presently, however, neither genomic sequencing nor an electrophoresis method, in general, are involved.

Yurov, Y. B. et al. (Human Genetics (1996) 97 (3) 390–8: High resolution multicolor fluorescence in situ hybridization using cyanine and fluorescein dyes: rapid chromosome identification by directly fluorescently labeled alphoid DNA probes) concerns the use of Cy3 and Cy5-dCTP for labeling purposes.

U.S. Pat. No. 5,837,832 describes arrays of oligonucleotides and their hybridization to sample DNA. However, either DNA methylation is not detected or the arrays described therein are not suitable for the hybridization of different fragments of complex amplifications so that they contain oligonucleotides complementary to the primers and thus specifically bind one fragment per oligonucleotide.

Different methods are known in the prior art, by means of which oligonucleotide arrays can be produced. They can be divided roughly into 3 groups:

1) All oligomers are prepared in the conventional manner individually and in relatively large quantities in special automated synthesis equipment and then individually pipetted onto the carrier. Automated, highly precise micropipette robot equipment is usually used for this purpose. The advantage of this method is that it is for the most part based on already optimized standard methods and equipment. Qualitatively superior DNA arrays with very pure oligomers can be produced in this way, which has an extremely positive influence on the detection sensitivity and reliability that can be obtained with the array. The great disadvantage of the method is that it is very time-consuming and is thus expensive.

2) The oligomers are synthesized by pipetting minimal quantities directly onto the substrate. The oligomer chain provided therein is constructed, nucleobase by nucleobase, at each grid point. For pipetting, as in method (1), a specialized micropipetting robot device is similarly used or, e.g., a device that contains channels for introducing the individual synthesis building blocks to the respective points of the array (EP-A-0915897). The chemical synthesis method is basically the same as for conventional oligomer synthesis in automated synthesis equipment.

3) The oligomers, as in method 2), are synthesized directly on the substrate, and the targeted binding of the correct nucleobases to the correct grid points is accomplished, however by a completely parallel photolithographic technique originating from semiconductor manufacture, instead of sequential, precisely targeted pipefting steps. The method is based on the fact that the 5'-OH protective groups can be removed from oligonucleotides in a targeted manner with light of a specific wavelength. By suitable local irradiation patterns, oligonucleotide ends can thus be made reactive at precisely those grid points at which it is desired that a new nucleotide building block will bind in the next step. When the array surface is completely wetted with a nucleotide building block solution, a nucleobase will thus be bound only at the previously exposed sites, and all of the unexposed sites will remain unchanged. The local exposure patterns are produced by positioning a photomicrograph black-and-white mask between the substrate and the light source that covers all grid sites, which will not be made reactive.

Due to the high parallel nature in processing, this method is very rapid and efficient, and it is also well suitable for the purpose of achieving very high grid densities, due to the high precision that can be obtained with photolithography.

An overview of the prior art relative to oligomer array production can also be taken from the special publication that appeared in January 1999 of Nature Genetics (Nature Genetics Supplement, Vol. 21, January 1999) and the literature cited therein.

Prior art, which generally concerns the use of oligomer arrays and photolithographic mask designs, includes, e.g., U.S. Pat No. 5,837,832; U.S. Pat. No. 5,856,174, WO98/27430 and U.S. Pat No. 5,856,101.

The amplification by DNA by means of PCR is prior art.

SUMMARY OF THE INVENTION

The object of the present invention is thus to create a method for the relative quantification of cytosine methylations in genomic DNA samples, which overcomes the disadvantages of the prior art.

The object is solved in that a method for the relative quantification of methylation of cytosine bases in DNA samples is made available, wherein the following method steps are conducted:

a) a genomic DNA sample is reacted chemically with a reagent, wherein 5-methylcytosine and cytosine react differently and after the reaction, these display a different base pairing behavior in the DNA duplex;

b) DNA samples are amplified, whereby a fluorescently labeled dCTP or cGTP derivative is added;

c) the amplified products are separated spatially from each other; and d) the fluorescence of the separated amplified products is quantitatively measured.

According to a preferred embodiment of the present method the amplified DNA sample is hybridized to one or more immobilized oligomers, whereby the immobilized oligomers hybridize at least to one of the primers or their complementary sequences used in the amplification step, whereby the spatial separation in the sense of step (c) is achieved.

According to a further preferred embodiment of the method according to the invention the separation in the sense of step (c) is performed by electrophoresis or chromatography. It is especially preferred to use capillary gel electrophoresis or high pressure liquid chromatography (HPLC).

In connection with the present invention the term hybridization comprises the formation of a DNA double helix in the sense of a Watson-Crick base pairing reaction from two single strand DNA molecules, whereby at least 75% of the base pairs within any sequence formed by 10 successive bases do not form a mispairing in the sense of a Watson-Crick pairing.

DETAILED DESCRIPTION OF THE INVENTION

According to the invention it is preferred that the sample DNA is taken from serum or other liquid of a living body.

It is further preferred that the sample DNA is taken from cell lines, blood, sputum, feces, urine, serum, cerebrospinal fluid, tissue embedded in paraffin, e.g. tissue from eyes, intestine, kidney, brain, heart, prostate, lung, breast or liver, histological slides and any combination thereof.

As described above, the method comprises the following steps:

a) a genomic DNA sample is chemically reacted with a reagent, wherein 5-methylcytosine and cytosine react differently and these thus show a different base pairing behavior in the DNA duplex after the reaction;

b) the DNA sample is amplified, whereby a fluorescently labeled dCTP or dGTP derivative is added;

c) the amplified products are separated spatially from each other; and d) the fluorescence of the separated amplified products is quantitatively measured.

In an especially preferred embodiment of the method according to the invention the amplified DNA sample is hybridized to one or more immobilized Oligomers, whereby the immobilized oligomers hybridize at least to one of the primers or their complementary sequences used in the amplification step in order to achieve the spatial separation in the sense of step (c).

In an further preferred embodiment the spatial separation in the sense of step (c) is achieved by electrophoresis or chromatography, especially preferred by capillary gel electrophoresis or high pressure liquid chromatography (HPLC).

It is preferred according to the invention that a bisulfite solution is used as the reagent in step a). It is also preferred that the treatment with bisulfite solution is carried out after embedding the DNA in agarose. It is also preferred that during the chemical treatment a DNA duplex denaturating agent and/or a radical scavenger is present.

In addition, it is preferred that PCR (polymerase chain reaction) is utilized for the amplification in step b). Further amplification reactions that can be used according to the invention are isothermic amplification, primer extension reactions, rolling-circle amplification, ligase chain reactions (LCR) and all other amplification reactions known the one skilled in the art.

According to the invention, it is particularly preferred that the fluorescently labeled dCTP or dGTP derivative in step b) is Cy3-dCTP, Cy5-dCTP, Cy3-dGTP or Cy5-dGTP. Further preferred fluorescence labels are for example TAMRA, ROX, JOE, TET or flourescein.

In addition, it is particularly generally preferred according to the invention that the fluorescent dyes Cy3 and/or Cy5 are used as the label, e.g. Cy3-dCTP and Cy5-dGTP simultaneously.

It is further preferred according to the invention that an array of oligomers complementary to the primers of step (b) is used for the hybridization of the amplified products in step c).

It is further preferred according to the invention that an array of oligomers identical to the primers of step (b) is used for the hybridization of the amplified products in step c).

All oligonucleotides can be used according to the invention that hybridize to the used primers or their complementary oligonucleotides. In connection with the present invention the term hybridization means the formation of a DNA double helix in the sense of a Watson-Crick base pairing reaction from two single strand DNA molecules, whereby at least 75% of the base pairs within any sequence formed by 10 successive bases do not form a mispairing in the sense of a Watson-Crick pairing.

In an preferred embodiment of the present invention the separation of the amplified products is performed by capillary gel electrophoresis or HPLC. In both cases the conditions are chosen in a way that denaturation occurs. This is state of the art n both methods used. Because single strands are detected, one can elucidate the contents of C or G, respectively, directly from the intensity of the fluorescence. Thereby it is possible to determine the degree of methylation directly, because, for example, in one strand cytosine (C) is only present if the respective Cytosin was methylated in the genomic DNA sample prior to the bisulfite treatment. The same applies to Guanine (G) in the counter strand. The fluorescence measured is dependent in any method from the amount of the respective single strand. For the purposes of an internal calibration it is effective and especially preferred to provide the primer with a fluorescence label different from that used in the strand during the PCR. This label can be used during the assay directly for the determination of the amount of single strand, whereas the fluorescence derived from the incorporation of C or G can be compared to the one derived from the label of the primers. by this a quantification of the methylation can be measured by internal calibration.

The same applies to the separation via an array of oligomers. Using the label of the primer the amount of amplification products bound to any position on the array can be determined and can be set into correlation to the fluorescence dereived from the incorporated G or C. By this, the assay becomes unaffected by the concentration of the amplification products.

It is also preferred that the amplification of several DNA segments is conducted simultaneously in step (b). It is preferred that in a PCR reaction many fragments are formed simultaneously, i.e. a multiplex PCR is performed. Using bisulfite treated DNA leads to the advantage that due to the different G and C content of the two DNA strands a forward primer will never act as a reverse primer, whereby the multiplexing is made easier.

It is particularly preferred that the values measured in step d) are equilibrated with the fluorescence of other, analogously treated DNA samples and information is obtained in this way of the relative degree of methylation of different tissues or cell samples.

The invention thus describes a method for the relative quantification of cytosine methylation in DNA samples. The DNA samples are treated chemically so that cytosine and methylcytosine react differently and only methylcytosine positions retain their base pairing behavior. The DNA is subsequently amplified, whereby the cytosine triphosphate or the guanosine triphospahte that is used is provided with a fluorescent label. If the fluorescence labels are different from each other, both nucleotides may be labeled. The fluorescently labeled nucleotides replace preferably the non labeled nucleotides in the amplification only partly. In the case of Cy5-dCTP the ratio with unlabeled dCTP in the PCR is preferably 1:3. Amplification protocols in order to solely achieve an internal labeling are state of the art. The amplified products are separated either by chromatography or gel electrophoresis or bound by specific hybridization to an oligomer on an array, and the solid phase is washed several times. When using an array, the fluorescence at the site of immobilization now provides preferably information on the relative number of cytosine methylations in the respective amplified DNA segment in comparison to other analogously treated samples. The hybridization of several different amplified products of a sample to an oligomer array, the fluorescence pattern of which now provides information on the methylation pattern in the DNA sample, is particularly preferred. The patterns of different samples are compared. It is especially preferred that an internal calibration using labeled primers is performed as described above.

The amplification of DNA by means of PCR is prior art. The use of fluorescence-labeled nucleotides for PCR according to the invention is particularly preferred. Thus, it is above all possible to introduce several fluorophores into one amplified product without a relatively expensive fluorescence labeling of primers. Cy5-dCTP (Cy5 is a commercially obtainable fluorescent dye) can be obtained from the company Amersham Pharmacia Biotech.

In other words, the invention thus describes a method for the quantification of cytosine methylation in DNA samples. The genomic DNA samples are first chemically treated in such a way that cytosine and methylcytosine react differently and only methylcytosine positions retain their base pairing behavior. Preferably, treatment is conducted with a bisulfite solution, which reacts almost exclusively with cytosine nucleobases and converts these to uracil after alkaline hydrolysis. 5-Methylcytosine does not react under the same conditions. The conversion of C to U leads to a change in the base sequence at the non-methylated positions. Subsequently, the DNA is amplified, whereby the triphosphate, e.g. cytosine triphospahte, that is used is provided with a fluorescent label. Preferably, Cy5-dCTP (Pharmacia) is used here. A Cy5-C and thus a fluorescent label can be incorporated in PCR only at those positions at which a conversion of C to U has not occurred. Thus, the number of incorporated Cy5-d CTPs is in good approximation proportional to the extent of methylation in the amplified DNA segment. Now Cy5-Cs will also be incorporated in the opposing strand at those sites, where a guanine has been found in the bisulfite-treated strand. This incorporation, in principle, interferes with the detection of fluorescence. This problem is surmounted in the present invention in that only relevant single strands from the solution are bound to the solid phase. After a step of thermal denaturation, they are bound by hybridizing to an immobilized oligomer that is complementary to at least one primer, and then the solid phase is washed several times. Optionally, the strands are separated by means of denaturating gel electrophoresis or chromatographic methods. The intensity of the fluorescence at the site of immobilization or during the detection now provides information on the relative number of cytosine methylations in the amplified DNA segment involved in comparison to other analogously treated samples. The hybridization of several different amplified products of a sample to an oligomer array, the fluorescence pattern of which now provides information on the methylation pattern in the DNA sample is particularly preferred. The oligomer array is preferably produced by introducing separately synthesized oligomers onto a carrier (chip) or by photolithographic techniques (prior art). The carrier material is preferably glass derivatized by silanizing.

The patterns of fluorescence of different samples are entered into a database and compared. Particularly preferred is the use of the method for obtaining information on the relative degree of methylation of various tissues of an individual and the same tissue of different individuals.

The following example of embodiment explains the invention:

EXAMPLE 1

Calibration of the Method for the Relative Quantification of Cytosine Methylation.

The following example of a method for the relative quantification of the methylation of cytosine bases in amplified nucleic acid fragments refers to fragments of multiple drug resistance (MDR1) and multi-resistance protein (MRP3) genes.

In the first step, glass substrates are chemically modified, so that a targeted binding of oligonucleotides can occur, as in the prior art. By introducing different types of oligonucleotides onto a substrate, oligonucleotide arrays can be prepared in the usual manner. For this purpose, the substrates are silanized, whereby the silane bears a functionalized alkyl chain.

Then the surface is provided with a bifunctional linker, for example, phenylene diisothiocyanate or adipic acid di(N-hydroxysuccinimidyl) ester. This linker permits a covalent binding of the oligonucleotides under basic conditions. In this case, the oliogonucleotides:

```
AAC TCC CCA ATA CTA CAA CC (MRP3)

AAAATACACAAACRCTCCCA (MRP3) and

CTACAATAATCTTTCTTCAACATACTTA (MDR1)

TAA AAA CTA TCC CAT AAT AAC TCC CAA C (MDR1),
``` which are complementary to the primers used in the amplification step, are introduced onto the substrate surface by automatic pipetting or spotting at defined positions.

Two methylated or unmethylated nucleic acid fragments (each of MDR1 and MRP3), by means of which unknown methylated samples can be compared, can be used for calibration for the relative quantification of the methylation of cytosine bases in nucleic acid fragments.

EXAMPLE 2

Preparation of Unmethylated Reference Sample

A genomic DNA sample (18 ng), which has been digested with the restriction enzyme Mss 1, is used in the case of the unmethylated sample. The first sample is amplified over 40 cycles with the use of 25 pmol of each of the specific primers:

```
CAAGCATGCTGAAGAAAGACCACTGCAG        (MDR1)
TGGGAACTGTCCCATAATAACTCCCAAC        (MDR1)
``` using the following program: T=96.0° C., 10 m; T=96.0° C. 30 s; T=58.0° C. 1:15 min; T=72.0° C. 2 min; T=72.0° C., 15 min.

The second sample is amplified over 45 cycles also with 25 pmol of the specific primers:

```
GGC TGC AGC ACT GGG GAG CC          (MRP3)
GGC TCC CCA GTG CTG CAG CC          (MRP3)
``` and the following program: T=96.0° C., 10 min; T=96.0° C., 1 min; T=55.0° C., 45 s; T=72.0° C., 1:15 min, over T=72.0° C. 10 min. Both amplified products are converted chemically with bisulfite (=hydrogen sulfite, disulfite) and a free-radical scavenger at elevated temperature. The bisulfite reaction leads to the conversion of all unmethylated cytosine bases to uracil. In order to purify the modified amplified products, the latter are bound to a reversed phase C18 solid phase and freed of chemicals by washing. Then the DNA is eluted with a polar solvent, such as, e.g., acetonitrile or water. The alkaline hydrolysis of the amplified product treated with bisulfite is conducted directly prior to the repeated specific amplification in which the fluorescence-labeled nucleotide is utilized. Defined fragments with lengths of 633 bp (MDR1) and 640 bp (MRP3), which fluoresce due to the defined incorporation of Cy5-dCTP are amplified.

The two genes MDR1 and MPR3 are in turn amplified, with 25 pmole of each primer:

```
TAAGTATGTTGAAGAAAGATTATTGTAG        (MDR1),
TAAAAACTATCCCATAATAACTCCCAAC        (MDR1),
AACTCCCCAATACTACAAC                 (MPR3)
TGGGAGYGTTTGTGTATTTT                (MRP3)
``` and 0.5–0.75 mM cy5-dCTP in the PCR. The PCR is run under the following conditions: MDR1: T=96.0° C. 20 min; T=96.0° C. 30 s; T=54.6° C. 1:15 min; T=72.0° C. 2 min; T=72.0° C. 15 min, over 40 cycles; MRP3: T=96.0° C. 20 min; T=96.0° C. 30 s; T=61.70 ° C. 1.15 min, T=72.0° C. 2 min; T=72.0° C. 15 min, over 40 cycles.

EXAMPLE 3

Production of the Methylated Reference Sample

For the methylation of genomic DNA, 1 μg of DNA is incubated at 37° C. for one hour with 1 unit of methylase Sss 1. The enzyme is then deactivated. The methylated sample is digested with Mss1 and specifically amplified.

Both amplified products are chemically converted with bisulfite (=hydrogen sulfite, disulfite) and a free-radical scavenger at elevated temperature. The bisulfite reaction leads to the conversion of all unmethylated cytosine bases to uracil. For the purification of the modified amplified products, the latter are bound to a reversed phase C18 solid phase and freed of chemicals by washing. Then the DNA is eluted with a polar solvent such as, e.g., acetonitrile or water. Alkaline hydrolysis of the amplified products treated with bisulfite is conducted directly prior to the repeated specific amplification in which the fluorescence-labeled nucleotide is utilized. Defined fragments, as in Example 2, are amplified.

PCR is conducted with 25 pmole of each specific primer:

```
TAAGTATGTTGAAGAAAGATTATTGTAG        (MDR1),
TAAAAACTATCCCATAATAACTCCCAAC        (MDR1),
AACTCCCCAATACTACACC                 (MRP3),
TGGGAGYGTTTGTGTATTTT                (MRP3)
``` and 0.5–0.75 mM Cy5-dCTP.

EXAMPLE 4

Hybridization of the Amplified Products

The amplified products are fixed by hybridizing in a known way to the corresponding surface-bound oligomers complementary to the primers not containing cytosine and the solid phase is washed several times in order to remove non-complementary amplified products.

The amplified products bound to the surface-bound oligonucleotides (oligomer array), which are in this example, as in 1), the sequences:

```
AAC TCC CCA ATA CTA CAA CC          (MRP3),
AAAATACACAAACRCTCCCA                (MRP3) and
CTACAATAATCTTTCTTCAACATACTTA        (MDR1),
TAA AAA CTA TCC CAT AAT AAC TCC CAA C  (MDR1)
``` are detected on the basis of their fluorescence at 635 nm. A commercially available fluorescence scanner (e.g. Genepix 4000, Axon Laboratories) is used for this purpose.

EXAMPLE 5

Evaluation

After calibrating the system with the originally methylated and unmethylated reference samples, other samples can now be measured. If there are basic differences in the methylation of the different amplified products of the samples to be investigated, which are worked up corresponding to the unmethylated samples, but without a preliminary amplification of the genomic DNA, then it happens that specific points on the array show a clearly increased or reduced fluorescence relative to the other points, as long as the amplified products are present in comparable concentration in the individual samples to be investigated.

The problem of comparable concentrations, which leads to the fact that only relatively extreme differences can be detected for the most part in this way (which, of course, does occur in the case of an almost complete methylation of a CpG island), can be overcome by fluorescence labeling of the primer with another dye, e.g., Cy3). In this case, the sample preparation is exactly the same, only conducted with Cy3-labeled primers. The intensities at 532 nm (Cy3) at the individual points then serve first for the equilibration of the concentrations of the individual amplified products, before the relative quantification of the methylated cytosines is conducted at 635 nm (Cy5) in the individual amplified products. The Cy3 values thus serve as the correction factor. The type and manner of evaluation of fluorescence measurements is known to the person with average skill in the art.

What is claimed is:

1. A method for the relative quantification of the methylation of cytosine bases in DNA samples, said method comprising the steps of:
   a) chemically reacting a genomic DNA sample with a reagent, wherein 5-methylcytosine and cytosine react differently and these thus show a different base pairing behavior in the DNA duplex after the reaction;
   b) then, amplifying the chemically reacted DNA sample by PCR, said amplifying step comprising the use of a fluorescently labeled dCTP or dGTP derivative to yield amplified products, whereby several fluorophores are introduced into one amplified product;
   c) then, spatially separating the amplified products from each other;
   d) then, quantitatively measuring the fluorescence of the separated amplified products; and
   e) then, determining from the measured fluorescence the relative number of methylated cytosine bases that were present in the DNA sample prior to step a).

2. The method according to claim 1, further characterized in that the amplified DNA sample is hybridized to one or more immobilized oligomers, whereby the immobilized oligomers hybridize at least to one of the primers used in the amplification step or sequences complementary thereto in order to achieve the spatial separation.

3. The method according to claim 2, further characterized in that an array of oligomers complementary or identical to the primers of step (b) is used for the hybridizing of the amplified products in step (c).

4. The method according to claim 1, further characterized in that the amplified products from step (b) are separated by electrophoresis or chromatography.

5. The method according to claim 4, further characterized in that the separation is achieved by capillary gel electrophoresis.

6. The method according to claim 4, further characterized in that the separation is achieved by high pressure liquid chromatography (HPLC).

7. The method according to claim 1, further characterized in that a bisulfite solution is used in step (a) as the reagent.

8. The method according to claim 1, further characterized in that in step (b) the fluorescently labeled dCTP or dGTP derivative is Cy3-dCTP, Cy5-dGTP, Cy3-dGTP or Cy5-dGTP.

9. The method according to claim 1, further characterized in that the fluorescent dyes Cy3 and/or Cy5 are used as the label.

10. The method according to claim 1, further characterized in that the amplification of several DNA segments in step (b) is conducted simultaneously.

11. The method according to claim 1, wherein said determining step comprises comparing the fluorescence intensity from each of the separated amplified products with the fluorescence intensity of other, analogously treated DNA samples in order to ascertain the relative degree of methylation that was present in the DNA sample.

12. The method according to claim 1, further characterized in that fluorescently labeled primers are used in the amplification step, wherein their fluorescent labeling is different from that of the dCTP or dGTP derivatives.

13. A method for the relative quantification of the methylation of cytosine bases in DNA samples, said method consisting of the steps of:

a) chemically reacting a genomic DNA sample with a reagent, wherein 5-methylcytosine and cytosine react differently and these thus show a different base pairing behavior in the DNA duplex after the reaction;

b) then, amplifying the chemically reacted DNA sample, wherein said amplifying step comprises the use of a fluorescently labeled dCTP or dGTP derivative to yield amplified products;

c) then, spatially separating the amplified products from each other;

d) then, quantitatively measuring the fluorescence of the separated amplified products; and e) then, determining from the measured fluorescence the relative number of methylated cytosine bases that were present in the DNA sample prior to step a).

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Homo sapiens

<400> SEQUENCE: 1
aactccccaa tactacaacc                                                    20

<210> SEQ ID NO 2
<211> LENGTH: 20
<212> TYPE: DNA
<213> ORGANISM: Homo sapiens

<400> SEQUENCE: 2
aaaatacaca aacrctccca                                                    20

<210> SEQ ID NO 3
<211> LENGTH: 28
<212> TYPE: DNA
<213> ORGANISM: Homo sapiens

<400> SEQUENCE: 3
ctacaataat ctttcttcaa catactta                                           28

<210> SEQ ID NO 4
<211> LENGTH: 28
<212> TYPE: DNA
<213> ORGANISM: Homo sapiens

<400> SEQUENCE: 4
taaaaactat cccataataa ctcccaac                                           28

<210> SEQ ID NO 5
<211> LENGTH: 28
<212> TYPE: DNA
<213> ORGANISM: Homo sapiens

<400> SEQUENCE: 5
caagcatgct gaagaaagac cactgcag                                           28

<210> SEQ ID NO 6
<211> LENGTH: 28
<212> TYPE: DNA
<213> ORGANISM: Homo sapiens

<400> SEQUENCE: 6
tgggaactgt cccataataa ctcccaac                                           28
```

```
<210> SEQ ID NO 7
<211> LENGTH: 20
<212> TYPE: DNA
<213> ORGANISM: Homo sapiens

<400> SEQUENCE: 7
ggctgcagca ctggggagcc                                                    20

<210> SEQ ID NO 8
<211> LENGTH: 20
<212> TYPE: DNA
<213> ORGANISM: Homo sapiens

<400> SEQUENCE: 8
ggctccccag tgctgcagcc                                                    20

<210> SEQ ID NO 9
<211> LENGTH: 28
<212> TYPE: DNA
<213> ORGANISM: Homo sapiens

<400> SEQUENCE: 9
taagtatgtt gaagaaagat tattgtag                                           28

<210> SEQ ID NO 10
<211> LENGTH: 19
<212> TYPE: DNA
<213> ORGANISM: Homo sapiens

<400> SEQUENCE: 10
aactccccaa tactacaac                                                     19

<210> SEQ ID NO 11
<211> LENGTH: 20
<212> TYPE: DNA
<213> ORGANISM: Homo sapiens

<400> SEQUENCE: 11
tgggagygtt tgtgtatttt                                                    20
```